(12) United States Patent
Daumüller

(10) Patent No.: US 8,690,038 B2
(45) Date of Patent: Apr. 8, 2014

(54) SURGICAL INSTRUMENT WITH GEARING

(75) Inventor: Thomas Daumüller, Below (DE)

(73) Assignee: Wenzler & Co., Balgheim (DE)

( * ) Notice: Subject to any disclaimer, the term of this patent is extended or adjusted under 35 U.S.C. 154(b) by 459 days.

(21) Appl. No.: 12/620,763

(22) Filed: Nov. 18, 2009

(65) Prior Publication Data
US 2010/0140319 A1    Jun. 10, 2010

(30) Foreign Application Priority Data

Nov. 18, 2008    (DE) ............... 20 2008 015 256 U

(51) Int. Cl.
*A61B 17/068*    (2006.01)

(52) U.S. Cl.
USPC ........................ 227/175.1; 227/19

(58) Field of Classification Search
USPC .................. 227/175.1–182.1, 19
See application file for complete search history.

(56) References Cited

U.S. PATENT DOCUMENTS

| | | | | |
|---|---|---|---|---|
| 4,400,170 | A | * | 8/1983 | McNaughton et al. ......... 604/62 |
| 5,273,519 | A | * | 12/1993 | Koros et al. ................ 606/83 |
| 5,336,229 | A | * | 8/1994 | Noda ....................... 606/144 |
| 5,437,681 | A | * | 8/1995 | Meade et al. .............. 606/145 |
| 5,465,895 | A | | 11/1995 | Knodel et al. |
| 5,527,320 | A | * | 6/1996 | Carruthers et al. ......... 606/143 |
| 5,527,322 | A | * | 6/1996 | Klein et al. .............. 606/144 |
| 5,653,713 | A | * | 8/1997 | Michelson ................. 606/83 |
| 5,792,074 | A | | 8/1998 | Turkel et al. |
| 5,797,958 | A | * | 8/1998 | Yoon ....................... 606/207 |
| 6,699,255 | B1 | | 3/2004 | Cushchieri et al. |
| 7,029,480 | B2 | * | 4/2006 | Klein et al. .............. 606/144 |
| 7,159,750 | B2 | * | 1/2007 | Racenet et al. ........... 227/180.1 |
| 7,559,449 | B2 | * | 7/2009 | Viola ....................... 227/175.1 |
| 7,588,175 | B2 | * | 9/2009 | Timm et al. .............. 227/179.1 |
| 7,810,690 | B2 | * | 10/2010 | Bilotti et al. ............. 227/175.1 |
| 2004/0102783 | A1 | * | 5/2004 | Sutterlin et al. ........... 606/80 |
| 2008/0237298 | A1 | | 10/2008 | Schall et al. |
| 2010/0038403 | A1 | * | 2/2010 | D'Arcangelo ............. 227/180.1 |

FOREIGN PATENT DOCUMENTS

DE    28 08 911 B1    3/1979

OTHER PUBLICATIONS

German Search Report, Pat. Appln. No. 09014336.3-2310, 7 pages, English translation, 2 pages.
EP Pat. No. 09 014 336.3, Response to European Patent Office and amended claims, 7 pages.

(Continued)

*Primary Examiner* — Brian D Nash
(74) *Attorney, Agent, or Firm* — Andrew F. Young, Esq.; Lackenbach Siegel, LLP

(57) ABSTRACT

The invention is a surgical instrument comprising a first toothed rack which can be pushed, in a linear manner, via a gear pair. The pushing causes an oppositely running linear movement of a slide, thereby opening and closing the surgical instrument. The first toothed rack is capable of being moved in a linear manner into a handle piece, or pulled out from the handle piece, via the corresponding movement of a lever. The lever is pivoted in the handle piece, and opened by a spring pair. A first gear and a second gear form the gear pair, and a size ratio of the gears determines the step-up, or the step-down, ratio of the surgical instrument. A cover guides the first toothed rack and the gear pair laterally and holds them in engagement. A screen protects the second toothed rack and the slide against damage.

6 Claims, 3 Drawing Sheets

(56) References Cited

OTHER PUBLICATIONS

Co-Pending, Allowed, EP Pat. No. 09 014 336.3, EPO Communication 71(3) Intention to Issue—notice of allowance, dated Oct. 6, 2011, with hand-marked-up-claim 1 by the EPO (for allowance), and images and reasons for allowance (11 pages in German); and English language translation thereof, with as-amended English claims 1-5 (absent drawings) (11 pages).

* cited by examiner

SURGICAL INSTRUMENT WITH GEARING

CROSS REFERENCE TO RELATED APPLICATIONS

This application is related to, and claims priority from, German Patent Application Serial No. 20 2008 015 256.9, filed Nov. 18, 2008, the entire contents of which is incorporated herein by reference.

BACKGROUND OF THE INVENTION

1. Field of the Invention

The present invention relates to a surgical instrument with gearing for maximizing the opening aspect of the instrument. More specifically, the present invention relates to a surgical instrument, which allows the surgeon to implement a large working pathway with the opening and closing of the surgeon's hand based upon the use of a gear transmission.

2. Description of the Related Art

The related art involves surgical instruments that can be opened and closed by lever ratios or toothings. The problem with these instruments is that the surgeon requires the largest possible opening of the instruments, but they are greatly limited by the pathway of the hand and the lever ratios of the instruments.

What is not appreciated by the prior art, relative to these instruments, is that the surgeon requires the largest possible opening of the instruments; but, they are greatly limited by the pathway of the hand and the lever ratios of the instruments.

Accordingly, there is a need for an improved surgical instrument wherein the largest possible opening of the instrument is optimally achieved.

ASPECTS AND SUMMARY OF THE INVENTION

One aspect of the present invention is to provide an improved surgical instrument wherein the largest possible opening of the instrument is optimally achieved through the use of a geared transmission.

The present invention relates to a surgical instrument comprising a first toothed rack which can be pushed, in a linear manner, via a gear pair. The pushing causes an oppositely running linear movement of a slide, thereby opening and closing the surgical instrument. The first toothed rack is capable of being moved in a linear manner into a handle piece, or pulled out from the handle piece, via the corresponding movement of a lever. The lever is pivoted in the handle piece, and opened by a spring pair. A first gear and a second gear form the gear pair, and a size ratio of the gears determines the step-up, or the step-down, ratio of the surgical instrument. A cover guides the first toothed rack and the gear pair laterally and holds them in engagement. A screen protects the second toothed rack and the slide against damage.

According to an embodiment of the present invention there is provided a surgical instrument with a gearing. The surgical instrument comprises a first toothed rack wherein when the first toothed rack is pushed in a linear manner, via a gear pair, the pushing causes an oppositely running linear movement of a slide, thereby opening and closing the surgical instrument.

The above, and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
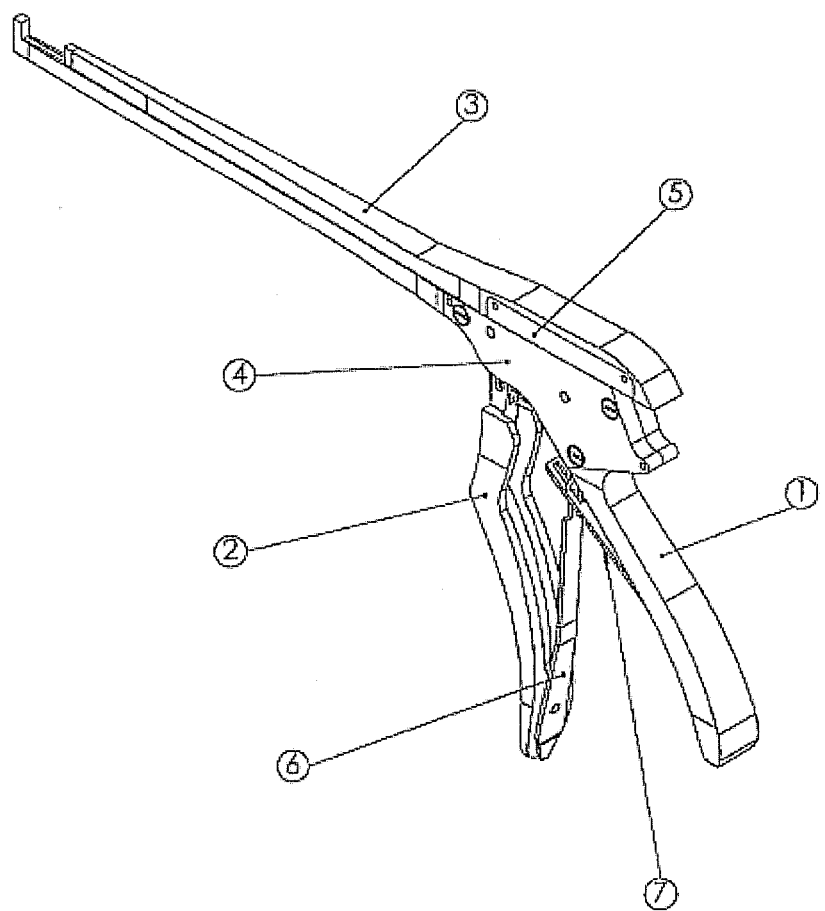
FIG. 1 is a perspective view of the surgical instrument with the handle piece and the lever at their most spread apart position, relative to each other, so as to allow the human hand to still enclose them.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

FIG. 1 shows the surgical instrument with the handle piece 1 and the lever 2, which are at their most spread apart position, relative to each other, via the springs 6 and 7, so as to allow the human hand to still enclose them.

The cover 4 protects the gearing, located in the handle piece 1, by which the slide 3 can be moved. The cover 4 guides the toothed rack 8 laterally, which is described more closely in the following FIG. 2. The screen 5 covers the toothed rack 13, which is firmly joined to the slide 3.

Figure 2:
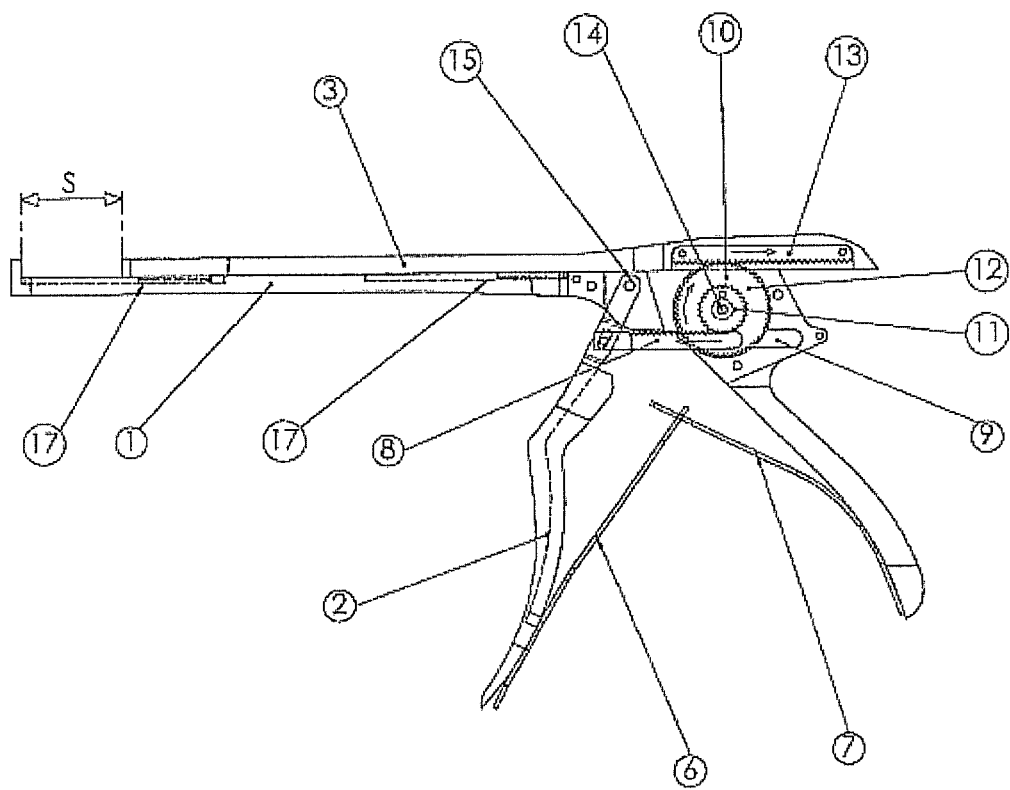
FIG. 2 is a perspective view of the surgical instrument, without the cover and the screen in place, and in the maximum opened state.

FIG. 2 shows the surgical instrument without the cover 4 and the screen 5 in the maximum opened state. The double arrow indicated as "S" shows this distance from handle piece 1 to slide 3. The distance corresponds to the working path of the surgical instrument.

The lever 2 is pivoted in the handle piece 1 by the lever axis 15. The handle piece 1 has a recess 9, in which the toothed rack 8 is guided in linear manner. A lengthwise hole 16 is made in the lever 2. The toothed rack 8 has a pin that is entrained in the lengthwise hole 16 of the lever 2.

The invention is characterized in that a pair of gears 10 is mounted in the handle piece 1 so that they can turn. The pair of gears 10 consists of the gear 11 and the gear 12, firmly joined to it. The two gears 11 and 12 are coaxially mounted in their center axis. The toothed rack 8 engages with the gear 11.

The springs 6 and 7 open the angle between lever 2 and handle piece 1 as far as possible by their spring force. The toothed rack 8 moves in linear manner with the lever 2, since it is guided in the recess 9. The pair of gears 10 is turned by the linear movement of the toothed rack 8 and for its part shoves the slide 3, by the toothed rack 13, in a direction opposite the movement of the toothed rack 8.

The guides 17 can be designed as groove guides, swallowtail guides, etc. They make sure that handle piece 1 and slide 3 are joined in parallel sliding fashion to each other.

Figure 3:
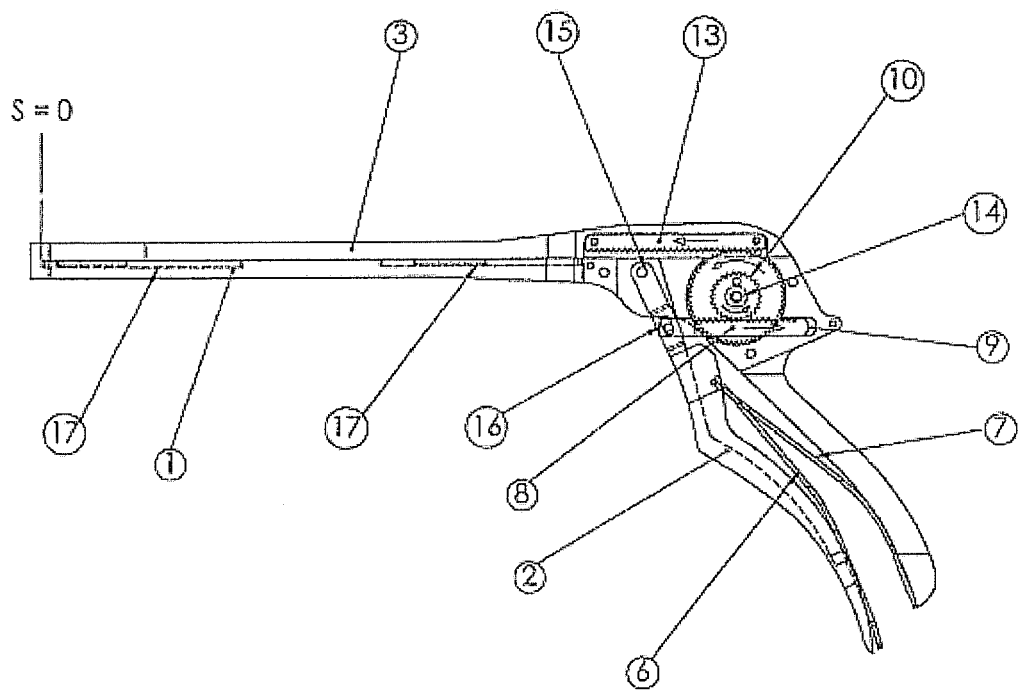
FIG. 3 is a perspective view of the surgical instrument, without the cover and the screen in place, while in a closed position.

FIG. 3 shows the closing of the instrument. The surgeon's hand moves the lever 2, which is pivoted in the handle piece 1 by the lever axis 15, against the forces of the springs 6 and 7.

The toothed rack 8 is shoved in linear manner into the handle piece 1. The direction of movement is indicated by the arrow on the toothed rack 8. Since the toothed rack 8 engages with the gear 11 of the gear pair 10, the gear pair 10 is turned about the gear axis 14. The turning motion of the gear pair 10 is transferred from the gear 12 across the toothed rack 13, which is firmly connected to the slide 3. The slide 3 closes the path S, indicated in FIG. 2, in a linear manner, contrary to the direction of the toothed rack 8. This closing motion is indicated by the arrow on the toothed rack 13.

In the claims, means or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A surgical instrument with a gearing, wherein: a linearly inserted rack produces via a gear pair an opposite linear movement of a slide whereupon the instrument is open and closed; characterized in that the rack is linearly inserted into a handle and pulled out by means of a lever; a gear A and a gear B form a gear pair firmly joined together, wherein the size ratio of the gear A and the gear B determines a transmission ratio and a reduction ration of the instrument; and characterized in that the gear pair is operably mounted in the handle and able to turn; a rack B is firmly joined to the slide; the lever is mounted in the handle and can turn and is opened by a spring pair; a cover laterally guides a rack A and the gear pair and fixably holds the rack A and the gear pair in operative engagement; and characterized in that a diaphragm protects the rack B of the slide.

2. A surgical instrument with a gear mechanism, in which a toothed rack (8) inserted in a linear manner causes a linear movement of a slide (3) in an opposite direction by way of a toothed wheel A (11) and a toothed wheel B (12), as a result of which the surgical instrument is operatively opened and closed respectively, wherein: a toothed rack B (13) is connected to the slide (3) in a fixed manner, characterized in that a toothed rack A (8) is operatively inserted into a handle member (1) or is withdrawn therefrom in a linear manner by way of a lever (2), and the toothed wheel A (11) and the toothed wheel B (12) form a pair of toothed wheels (10) connected to each other in a fixed manner, wherein the size ratio of the toothed wheel A and the toothed wheel B fixes a gear ratio of the instrument.

3. An instrument according to claim 2, characterized in that:
the pair of toothed wheels (10) are mounted in the handle member (1) in a rotatable manner.

4. An instrument according to claim 3, characterized in that:
the lever (2) is mounted in the handle member (1) in a rotatable manner and is opened by a pair of springs (6/7).

5. An instrument according to claim 4, characterized in that:
a cover (4) guides the toothed rack A (8) and the pair of toothed wheels (10) laterally and secures a continued engagement thereof.

6. An instrument according to claim 5, characterized in that:
a screen (5) protects the toothed rack B (13) of the slide (3) from dirt and the risk of damage.

\* \* \* \* \*

UNITED STATES PATENT AND TRADEMARK OFFICE
CERTIFICATE OF CORRECTION

PATENT NO.        : 8,690,038 B2
APPLICATION NO.   : 12/620763
DATED             : April 8, 2014
INVENTOR(S)       : Thomas Daumüller It is certified that error appears in the above-identified patent and that said Letters Patent is hereby corrected as shown below:

On the Title Page

Item (75) Inventor: Thomas Daumüller, "Below (DE)" should be changed to
-- Leinfelden-Echterdingen (DE) --

Signed and Sealed this
Third Day of June, 2014

Michelle K. Lee
*Deputy Director of the United States Patent and Trademark Office*